United States Patent [19]

Hyman

[11] 4,161,283

[45] Jul. 17, 1979

[54] ARTICLE FOR THE DISPENSING OF VOLATILES

[76] Inventor: Sy Hyman, 425 E. 58 St., New York, N.Y. 10022

[21] Appl. No.: 803,369

[22] Filed: Jun. 3, 1977

[51] Int. Cl.² ............................................. A61L 9/04
[52] U.S. Cl. .................................................... 239/55
[58] Field of Search ........................ 239/34, 36, 53–56

[56] References Cited

U.S. PATENT DOCUMENTS

| | | | |
|---|---|---|---|
| 2,615,754 | 10/1952 | Lindenberg | 239/56 X |
| 2,717,174 | 9/1955 | Casanovas | 239/56 |
| 3,343,664 | 9/1967 | Poitras | 239/56 X |
| 3,575,345 | 4/1971 | Buck, Jr. | 239/34 |
| 3,685,734 | 8/1972 | Paciorek | 239/56 |
| 3,785,556 | 1/1974 | Watkins | 239/34 X |
| 3,815,828 | 6/1974 | Engel | 239/56 |
| 3,844,478 | 10/1974 | Davis | 239/57 |
| 3,896,995 | 7/1975 | Lelicoff | 239/56 X |

*Primary Examiner*—Robert W. Saifer

*Attorney, Agent, or Firm*—Stephen E. Feldman; Marvin Feldman

[57] ABSTRACT

An article for the slow release of volatilizable substances, such as deodorizers, insecticides, repellants and the like, the article being formed from opposed outer and inner wall members joined along their peripheral portions to define a central reservoir portion for receiving and confining a volatilizable substance. The outer wall member comprises a non-porous flexible polymeric sheet material which does not permit bulk flow, but allows molecular diffusion therethrough. The inner wall member comprises an impermeable barrier layer. Another barrier layer is releasably bonded to the outer wall and prevents escape of volatilizable substance until its removal at the time of desired use. In a further aspect, a strippable adhesive layer is bonded to the outer surface of the inner wall impermeable layer and removal of the strippable layer enables adhesive bonding of the article to environmental surfaces.

19 Claims, 4 Drawing Figures

ARTICLE FOR THE DISPENSING OF VOLATILES

BACKGROUND OF THE INVENTION

1. Field of the Invention

The invention relates generally to an article of manufacture for the slow release of a volatilizable substance such as deodorizing means, insecticides, repellants, perfumes, medicaments and the like.

2. Description of the Prior Art

Articles of diverse types for the regulated, incremental release of a volatilizable substance over a period of time are well known in the art. Wick-type deodorizer dispensers having a stem portion retractably extensible from its container at the manipulation of the user to expose a fresh increment of volatilizable deodorizer as needed. Though effective under limited conditions, such dispensing devices entail many objectionable aspects. The outer containers of such dispensing devices are bulky, and are highly visible in use, often producing esthetically displeasing effects that clash with surroundings. Also such devices are often difficult to manipulate. Moreover, the immersed impregnated wick is directly exposed to the surrounding variable ambient conditions and relative humidity which often leads to unpredictable and often unduly accelerated volatilizing into the surrounding environment.

Envelope type or packet containers having an adsorbent pad saturated and a scented member disposed and likewise entensibly retractable to predetermined positions of projection are similarly objectionable. In either case, the whim of the user is the ultimate criteria for determining the rate and amount of scented vapor to be dispensed.

Representative prior art in this regard includes, for example, U.S. Pat. No. 3,575,345 which describes a deodorizer dispensing packet comprising opposed front and back sheets sealed together along their peripheral portions, each of the sheets preferably comprising an aluminum foil layer sandwiched between an inner polyethylene layer and an outer paper layer. Within the sealed enclosure is disposed an absorbent material, preferably porous paper impregnated with perfume. The packet is structurally adapted to be torn horizontally whereby to open the packet and enable withdrawal of the internally disposed impregnated porous paper for direct exposure to the surrounding atmosphere. An adhesive stripping is provided on one surface of the packet permitting its attachment to a suitable surface. Thus, the barrier foil layers are not removably attached and dispensing of the scented vapors is made possible only by tearing open the packet, the structure being so adapted. This device is thus similar to the "wick" type dispensers previously discussed hereinbefore.

Molded plastic box type dispensing means was more recently promulgated in the art, but proved only partly remedial. In the case of the molded plastic box type dispensers, such as household "air fresheners", the effective surface area available to pass vapor is limited since only the facing surface is exposed to the atmosphere. Moreover, these articles are likewise of rather bulky construction, difficult to manipulate and relatively costly to manufacture and assemble.

U.S. Pat. No. 3,844,478 describes a block of deodorizing material such as a wax impregnated with a deodorizing substance. Removable protective coverings are provided on opposed surfaces of the block. An adhesive coating may also be provided on the rearward surface overcoated with the protective covering. A rigid plastic plate acting as a barrier may be interposed between the block and adhesive layer. This patent describes a rigid plastic cage structure in which having side and end walls and a foraminous surface through which vapors escape.

U.S. Pat. No. 3,815,828 describes a sealed envelope structure for containing liquid emulsions or impregnated pads for dispensing vapors to the atmosphere. In this patent, vapor release occurs through all surfaces of the envelope. Neither barrier layers nor adhesive means for attaching the envelope to a surface are described.

U.S. Pat. No. 3,702,677 describes a vapor dispensing device comprising a rupturable container containing a scented material disposed within a paper container. The device is activated by pressing the envelope in a manner to cause rupture of the internally disposed container. The paper container, being porous to liquids, allows the scented material to flow thereoutof.

It is a principle object of this invention to provide an article for dispensing volatilizable substances from within the article to the surrounding environment at the desired time of use.

An object of the present invention is to provide an article capable of dispensing volatilizable substance emanating from a liquid semi-solid (gel), or solid source, in regulated, linear quantities over a prolonged period of time.

Still another object of the invention is to provide such an article embodying structural features enabling efficient utilization of volatilizable substances and only at time of desired use.

A further object of the invention is to provide such an article wherein loss of volatilizable substance through premature dispensing thereof is avoided before desired use and minimized in actual use.

It is another object of this invention to provide a slow vapor release from the surface of the article wherein there is a linear rate of release of the vapor to the surrounding atmosphere.

It is a further object of this invention to provide a slow vapor release article which effectively and efficiently utilizes each unit of vaporizable substance contained in the article.

A still further object of the invention is to provide such an article embodying structural features enabling its positioning on a variety of environmental surfaces.

Yet a still further object of the invention is to provide such an article having an arrangement of parts conducive to efficient mass production and relatively inexpensive manufacture.

Other objects and advantages of the invention will become more apparent hereinafter as the description proceeds.

Broadly speaking, the article of this invention is an outer layer of polymeric material bonded to an inner layer of barrier material along their peripheral portions to define a reservoir portion for containing a volatilizable substance, and a second barrier layer releasably secured to the outer polymeric layer, whereby the volatilizable material is contained within the reservoir until the second barrier layer is removed to permit the volatilizable material to disperse from the exposed surface of the polymeric material to the surrounding atmosphere.

In other words, the present invention provides an article for the controlled slow dispersion of a volatilizable substance to the surrounding atmosphere which comprises a sealed pouch joined along the periphery to define a substantially centrally disposed reservoir portion for containing a volatilizable liquid substance, with the outer wall of the pouch comprising a non-bulk flow, molecular dispersion permitting polymer and a barrier layer removably bonded to and completely covering the outer surface thereof, whereby the barrier layer prevents migration of volatilizable substance to the surrounding atmosphere until the barrier type is removed from the polymer layer.

The invention is described but not limited by reference to the accompanying drawing herein:

DETAILED DESCRIPTION OF THE INVENTION

Figure 1:
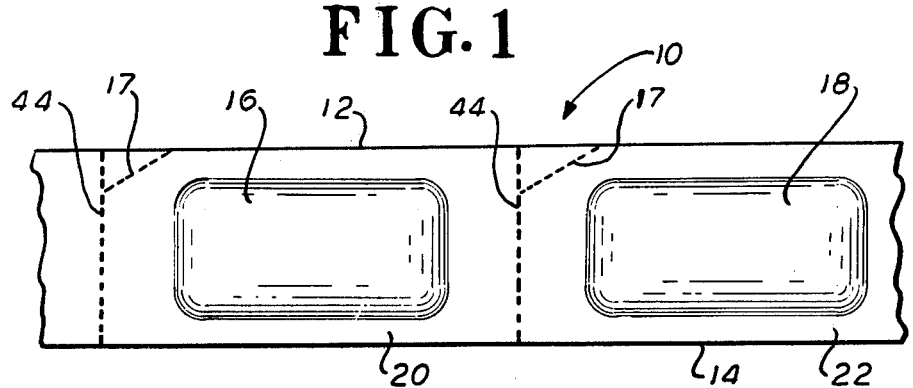
FIG. 1 is a plan view shown partly broken away illustrating one embodiment of the invention.
Figure 2:
FIG. 2 is a side elevational view of the embodiment of FIG. 1.
Figure 3:
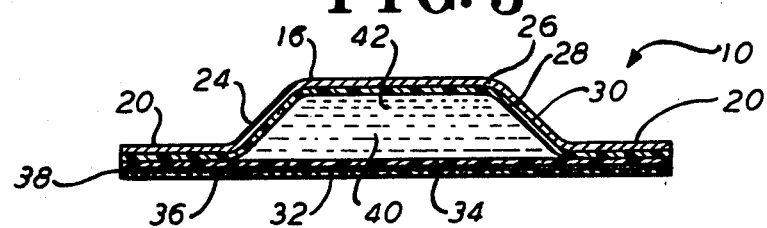
FIG. 3 is a sectional view taken along the line 3—3 in FIG. 2.

In the following description like reference numerals designate similar parts throughout the several views and wherein 10 generally designates an article in accordance with the invention, the embodiment of FIG. 1 depicting an elongated strip material having opposed longitudinal edges 12 and 14 provided with pouch or envelope portions 16 and 18 surrounded by rim portions 20 and 22, respectively. The construction is illustrated in more detail in FIG. 3. Outer wall member 24 comprises a first barrier layer 26 which completely overlies polymeric layer 28 being removably adhered thereto. Barrier layer 26 may be of a variety of materials but is most preferably thin metal foil such as aluminum foil. It is essential in the present invention that barrier layer 26 be impermeable to molecular diffusion, as will be described in detail hereinafter. Materials other than metal foil such as a wide variety of plastic materials, may be effectively used provided such material have the defined impermeability characteristics and particularly within the temperature-humidity ranges encountered in the intended use. For example, as regards deodorizing applications in accordance with the invention, moderate temperatures normally characteristic of household applications would be encountered; however, in accordance with other embodiments of the invention, e.g., the use of the article as a deodorizer, sanitizer, etc. to be added to the drying cycle of a clothes laundering operation, the temperatures would be quite higher. Thus, the chemical nature of barrier 26 depends on the ultimate utility contemplated, and selection of this material has necessary reference thereto.

Polymeric materials useful in preparing layer 28 may be selected from a relatively wide range of substances, e.g., polymers and interpolymers derived the polymerization of one or more ethylenically unsaturated monomeric materials, i.e., the vinyl monomers. The polymeric materials are esssentially water insoluble, i.e., hydrophobic. In addition, such materials, in accordance with an essential aspect of the invention, while not permitting bulk flow will nevertheless allow molecular diffusion of the volitilizable liquid material confined within reservoir 16. A particularly preferred polymer of the vinyl type if polyvinyl chloride although polyethylene, polypropylene and the like, may be used. Polymers other than those of the vinyl tape may be used with advantage, these including, without necessary limitation, polyurethanes, polysiloxanes (silicones), thermoplastic elastomers, rubbers, etc. such as the product HYTREL. As was the case with reference to barrier layer 26, selection of a given polymer within the limitations expressed is controlled at least in part by the conditions to be encountered in the ultimate use contemplated. The molecular weight of the polymer material may be considered in the selection of the diffusion control layer. The thickness of polymer layer 28 will generally range between about 0.01 and 0.001 inch. In the case of metal foil, attachment thereof to polymer layer 28 may be achieved without adhesive; adhesive is also optional with the use of plastics for barrier layer 26, the requisite bonding being obtainable, for example, by heat seal or heat fusion.

It is to be borne in mind that while the metal foil prevents vapor release from the polymer surface to the atmosphere, some volatilizable substance fraction permeates the polymer diffusion layer and collects between the foil-polymer interface permitting more ready release and removal of the barrier foil from the polymer.

Inner wall member 32 comprises a second barrier layer 34 having a peelable backing strip 36 adhesively bonded thereto, the adhesive being represented at 38. Barrier layer 34 may be constructed of the same or different material as barrier layer 26. Again, the essential properties of such layer is impermeable and does not permit molecular diffusion. From a cost standpoint, paper is the preferred material for peelable layer 36 although a wide variety of materials such as film forming resinous polymers may be used. Adhesive layer 38 is preferably of the pressure sensitive type as is well known in the art.

Polymer diffusion layer 28 and barrier layer 34 are bonded to form a permanent union. This union is most effectively accomplished by heat-sealing or heat-fusion according to known techniques to form reservoir or supply portion 40 enclosed by rim portion 20. Reservoir portion 40 is adapted to contain and confine a volatilizable substance 42 which may be in liquid form, e.g., solution, emulsion, suspension, etc., or alternatively may comprise a solid or semi-solid material (not shown) such as a gel, wax, padding material and the like saturated or supersaturated with the volatile substance. Gel forms include blends of the liquid active volatilizable agents with gelling agents such as cab-o-sil, carinogen, carboxymethyl cellulose, zinc stearate, and the like. Polymer layer 28 can be set to the partly arcuate shape illustrated in FIG. 3, e.g., by molding, or alternatively, can be a resiliently flexible member which assumes the shape illustrated upon introduction of the volatilizable substance.

Suitable volatilizable substances useful in the construction herein described include perfumes, cosmetics, deodorizers, fragrances, anti-bacterial agents, anti-microbial agents, counteractants, insect control agents (e.g. insecticides, insect-repellants, attractants, and the like) corrosion-inhibitors, medicants and the like. Suitable perfumes include without necessary limmitation the essential oils of various fragrances, flower perfumes, e.g., lilacs, roses, etc., wood perfumes such as cedar, pine, briar, etc., fruit flavorings such as lemon, cherry, etc.

Medicinal volatiles include menthol, camphor, eucalyptus and the like; exemplary anti-bacterial agents include phenol, thymol, and the like.

In use, the consumer merely removes barrier layer 26 to "activate" the vapor dispensing article. For such purposes, a tab member 17 may be provided on layer 26. Removal of layer 26 exposes the surface of polymer layer 28 from which volatilizable substance 42 will escape into the surrounding atmosphere. The vapors are dispensed at a substantially linear rate over the entire extent of the exposed surface area of layer 28. Premature or inadvertent dispensing of the vapors is effectively prevented by virtue of barrier layer 26. Thus, until the time of actual use, barrier layer 26 remains in place at which time removal is effected by the consumer. If desired, layer 26 can be repositioned on the polymer layer and the volatilization from the surface discontinued until a later time.

In a further aspect of the invention, layer 36 can also be stripped from the article as desired by the consumer to expose adhesive layer 38. This adhesive backing enables the article to be attached to a variety of environmental surfaces such as tables, closets, bathroom surfaces, etc. Moreover, being of flexible, lightweight construction, it can readily be affixed to surfaces of arcuate configuration such as piping. This adaptability feature enables the article to be positioned in areas which would not ordinarily be readily visible and is thus of significant advantage from an esthetic standpoint. The use of perfume-containing articles is of particular value where it is desired to mask or neutralize objectionable scents such as those encountered in kitchens, bathrooms, closets and the like. The article may also be used to dispense vapors having therapeutic effects when inhaled and can accordingly be affixed to any suitable surface in the room where necessary.

As will be further noted, movement of the volatilizable substance is limited directionally, outwardly of the element through polymeric layer 28. Barrier layer 34 prohibits diffusion of volitilizable substance rearwardly of the element, which also protects the pressure sensitive adhesive layer from attack.

It is important that barrier layer 26 completely cover the outer reservoir surface of polymeric layer 28 so as to provide an effective seal.

As illustrated in FIG. 1, the article of the present invention may be provided in the form of an elongated strip comprising a plurality of such articles. Perforations 44 provided laterally of the connecting rim portions enable individual elements to be severed as desired. Alternatively, several connected elements can be used to provide an even greater supply of vapor to the surrounding atmosphere.

As previously mentioned, the volatilizable material may be in the form of a liquid, e.g., solution, suspension or emulsion, or in the form of a semi-solid or solid material impregnated with the volatilizable material. Thus, the emulsion form can be achieved with the use of a suitable solvent along with a surfactant material and/or a protective colloid such as polyvinyl alcohol, methyl cellulose and the like. Particularly effective surfactants include nonionic detergents derived from the polyoxyalkylation of alcohols. Impregnated waxes and fibrous materials may also be used.

The invention is particularly advantageous with respect to the use of a liquid material in reservoir 40.

One of the particularly valuable aspects of the invention relates to the fact that a relatively large volume of liquid containing high concentration of aromatic perfume, for example, is accommodated by the article reservoir relative to its total size, e.g., 3—4 grams of perfume concentrate per article. In addition, linear release of the perfume is achieved due to the constant concentration gradient of liquid material maintained within reservoir portion 40. This allows substantially uniform dispensing of the perfume ingredient over a prolonged period of use. This is to be contrasted with prior art devices and particularly those requiring adjustment on the part of the user as a given increment of available surface area sublimes and becomes depleted. Furthermore, the present articles are relatively inexpensive due to the simplicity of their construction, ease of continuous manufacture and the low cost types of polymeric materials required.

In the present invention, the hermetically sealed envelope type construction renders the article highly efficient as regards the use of highly concentrated liquid reservoir supplies.

Figure 4:
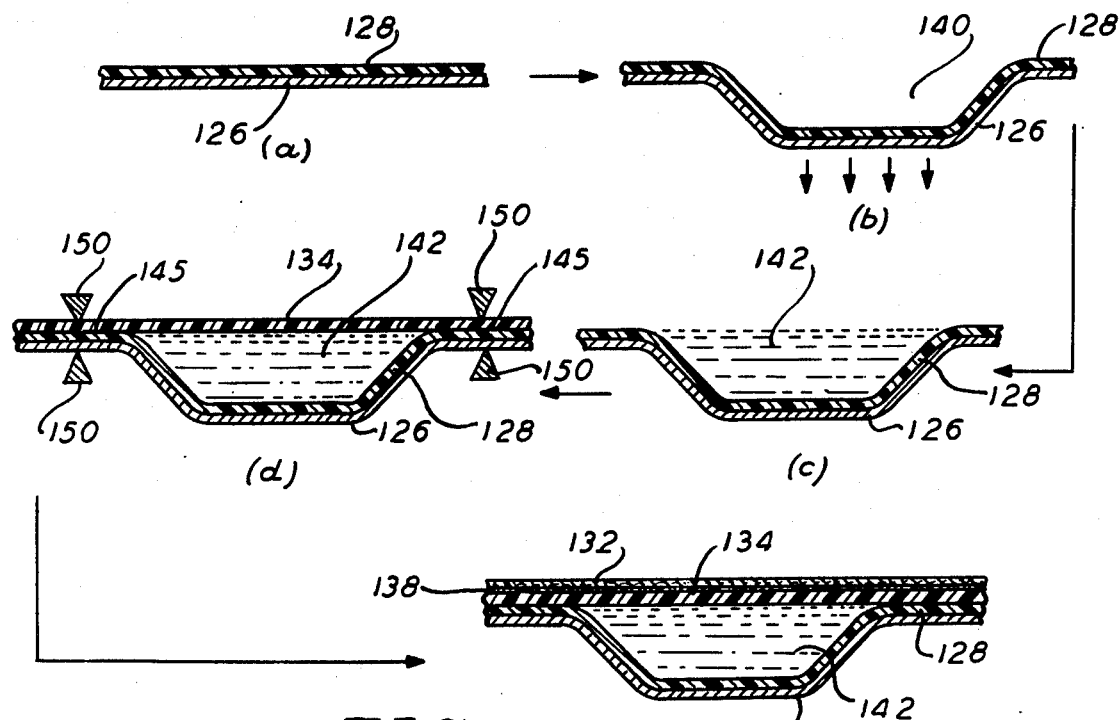
FIG. 4 is a process diagram depicting the step-wise method of forming the article of the invention.

Referring now to FIG. 4, there is shown a step-wise method of forming the article of the present invention. In step a., a continuous strip of the diffusion control polymer 128 bonded to the metal foil 126 is provided with the metal foil disposed below the polymer, and in step b. a pouch or reservoir 140 is formed in the strip by well-known pressure-forming or vacuum forming means (not shown). In step c., the volatilizable substance (e.g. liquid) 142 is placed in formed reservoir 140. Thereafter a strip of polymer barrier layer 134 is placed over the reservoir portion as well as over the face portions 145 of polymer diffusion layer 128, and a well-known heat-seal crimp mechanism 150 provides a peripheral heat-seal of polymer layers 134 and 128, and a crimp-seal of layer 128 to foil 126. Turning to step e., the article of step d. is further provided with a release paper strip 132 releasably bonded to polymer barrier layer 134 by an adhesive 138.

The present articles may be simply manufactured according to well known techniques. As stated, bonding of polymeric layer 28 and barrier layer 34 can be effected by simple heat sealing, heat-fusion or the use of adhesives. In the case of solid and semi-solid volatiles, fusion of layers 28 and 34 may be effected across the mass of volatilizable material. The remaining adhesive, barrier and peelable layers are then applied. Other techniques relevant to preparation of the present articles are described for example in U.S. Pat. Nos. 2,940,230; 2,793,481; 2,290,564; 3,020,687; 2,958,169; 2,998,176; 2,469,975; 2,802,324; 3,065,915 and 636,317.

The present invention has been described with respect to certain preferred embodiments thereof. However, it will be understood that changes and modifications may be made without departing from the scope thereof.

What is claimed is:

1. An article for the dispersion of a volatile substance to the surrounding atmosphere comprising opposed outer and inner wall members heat-sealed along their peripheral portions to define a substantially centrally disposed reservoir portion for containing a volatilizable liquid substance substantially filling said reservoir, said outer wall comprising a molecular diffusion polymer, a first barrier layer removably attached to and covering the outer surface thereof, said first barrier layer being substantially impervious to molecular diffusion, and said inner wall comprising a second barrier layer substantially impervious to molecular diffusion, and comprising a dissimilar polymer from the molecular diffusion polymer, whereby the removal of the first barrier layer from the outer wall permits dispersion of the volatilizable substance through the outer wall to the surrounding atmosphere.

2. The article according to claim 1, wherein said first barrier layer comprises metal foil.

3. The article according to claim 2, wherein said metal foil comprises aluminum foil.

4. The article according to claim 3 further comprising an adhesive disposed between the metal foil and the outer wall.

5. The article according to claim 1, wherein said molecular diffusion polymer layer is selected from the group consisting of vinyl polymers, polyolefins, polyurethanes, elastomers, and silicone polymers.

6. The article according to claim 5, wherein said molecular diffusion polymer comprises polyvinyl chloride.

7. The article according to claim 1, further comprising an adhesive layer, bonded to the face of the second barrier layer disposed away from said reservoir.

8. The article according to claim 7 wherein said adhesive is pressure sensitive.

9. The article according to claim 1, wherein said reservoir portion contains a volatilizable substance selected from the group consisting of perfumes, medicaments, insect control agents, corrosion inhibitors, deodorants and anti-germicidal agents.

10. The article according to claim 9, wherein said perfume is selected from the group consisting of essential oils, flower perfumes and fruit flavorings.

11. The article according to claim 1, wherein said second barrier layer comprises metal foil.

12. The article according to claim 11, wherein said metal foil comprises aluminum foil.

13. The article of manufacture comprising a plurality of articles as defined in claim 1, in the form of a unitary elongated strip.

14. The article according to claim 13, including laterally disposed perforations between said articles for expediting their removal from said strip.

15. The article according to claim 1, wherein said first barrier layer includes tab means for expediting removal of said layer from said article.

16. The article according to claim 1 wherein said first barrier layer is adhesively bonded to the outer surface of said molecular diffusion polymer layer.

17. The article according to claim 1, wherein said polymer is Mylar.

18. The article according to claim 1, wherein said outer wall prevents bulk flow from the reservoir.

19. An article for the dispersion of a volatile substance to the surrounding atmosphere comprising a layer of a molecular diffusion polymer and a layer substantially impervious to molecular diffusion, said layers being heat bonded to each other along their respective peripheral portions to form a reservoir portion for containing a liquid volatilizable substance, another layer substantially impervious to molecular diffusion overlying said molecular diffusion layer, whereby the liquid volatilizable substance may diffuse through the first said layer to the surrounding atmosphere.

* * * * *